(12) United States Patent
Niedzwiecki et al.

(10) Patent No.: US 11,986,507 B1
(45) Date of Patent: May 21, 2024

(54) MICRONUTRIENT COMPOSITION TO IMPROVE MEN'S HEALTH

(71) Applicant: Matthias W Rath, Henderson, NV (US)

(72) Inventors: Aleksandra Niedzwiecki, Henderson, NV (US); Matthias W Rath, Henderson, NV (US); Vadim O Ivanov, Castro Valley, CA (US)

(73) Assignee: Matthias W. Rath, Henderson, NV (US)

( * ) Notice: Subject to any disclaimer, the term of this patent is extended or adjusted under 35 U.S.C. 154(b) by 0 days.

(21) Appl. No.: 18/242,099

(22) Filed: Sep. 5, 2023

(51) Int. Cl.

| | | |
|---|---|---|
| *A61K 33/30* | (2006.01) | |
| *A61K 31/198* | (2006.01) | |
| *A61K 31/404* | (2006.01) | |
| *A61K 31/455* | (2006.01) | |
| *A61K 31/566* | (2006.01) | |
| *A61K 31/593* | (2006.01) | |
| *A61K 31/685* | (2006.01) | |
| *A61K 36/48* | (2006.01) | |
| *A61K 36/482* | (2006.01) | |
| *A61K 36/537* | (2006.01) | |
| *A61P 5/26* | (2006.01) | |
| *A61P 29/00* | (2006.01) | |

(52) U.S. Cl.
CPC .......... *A61K 36/537* (2013.01); *A61K 31/198* (2013.01); *A61K 31/404* (2013.01); *A61K 31/455* (2013.01); *A61K 31/566* (2013.01); *A61K 31/593* (2013.01); *A61K 31/685* (2013.01); *A61K 33/30* (2013.01); *A61K 36/48* (2013.01); *A61K 36/482* (2013.01); *A61P 5/26* (2018.01); *A61P 29/00* (2018.01)

(58) Field of Classification Search
CPC .......... A61K 8/67; A61K 31/375; A61K 8/63; A61K 31/455; A61P 15/00; A61P 21/00; A61P 3/02
See application file for complete search history.

(56) References Cited

U.S. PATENT DOCUMENTS

| | | | | |
|---|---|---|---|---|
| 9,216,184 B1 * | 12/2015 | Trunin | ................. | A61K 9/2013 |
| 2006/0204599 A1 * | 9/2006 | Wheat | .................... | A61K 36/53 |
| | | | | 514/649 |
| 2019/0167750 A1 * | 6/2019 | Damaj | .................... | A23L 33/15 |
| 2023/0346873 A1 * | 11/2023 | Pond | .................. | A61K 36/9068 |

OTHER PUBLICATIONS

Harvard Health, "Too much vitamin D may harm bones, not help", Harvard Health Publishing, a blog article retrieved on Nov. 18, 2023, retrieved from the internet: <URL: https://www.health.harvard.edu/staying-healthy/too-much-vitamin-d-may-harm-bones-not-help>, publication of Dec. 1, 2019 (Year: 2019).*

* cited by examiner

*Primary Examiner* — Robert T. Crow
*Assistant Examiner* — John P Nguyen
(74) *Attorney, Agent, or Firm* — Geeta Kadambi; RIDDHI IP LLC

(57) ABSTRACT

A micronutrient composition shown as Mix 1 comprises Rosemary extract at 1 mg-6,000 mg, Fenugreek extract 1 mg-50,000 mg and Fenugreek seed powder at 2 mg-8,000 mg, Cassia nomane seed extract powder 1 mg to 1,000 mg and dry extract 1 mg-300 mg, 3'3-di indolylmethylene 1 mg-800 mg, Zinc 0.1 mg-1,000 mg, Phosphatidylserine 1 mg-1,500 mg, Vitamin D 20 IU-10,000 IU, Vitamin C 10 mg-50,000 mg, Niacin 1 mg-3,000 mg, Theanine 0.1 mg-10,000 mg, Aspartic acid 10 mg-10,000 mg, Arginine 10 mg-50,000 mg and Dehydroepiandrosterone (DHEA) 1 mg-500 mg and Mix A comprising of all the ingredients of Mix 1 but does not contain DHEA and both are used improve men's health.

17 Claims, 15 Drawing Sheets

MICRONUTRIENT COMPOSITION TO IMPROVE MEN'S HEALTH

FIELD OF STUDY

The instant study is focused on a micronutrient composition that protects, improves and enhances men's health.

BACKGROUND

The male reproductive system consists of testes, the network of excretory and ejaculatory ducts, seminal vesicles and prostate, among others. Testes produce sperm and testosterone, which is the male sex hormone. Testosterone is responsible for the development of male sex organs and secondary sexual characters. It regulates spermatogenesis and libido in males. Testosterone also affects bone mass, fat distribution, muscle mass and strength.

Vascular tone is influenced by both the endothelium and vascular smooth muscle cells. The degree of smooth muscle contraction determines the diameter or tone of the vessel and is regulated at many levels. Widening of blood vessels is a result of the relaxation of the blood vessel's muscular walls. This enhances blood flow to areas of the body thereby providing oxygen and nutrients. It has been shown that among other factors physiological testosterone levels have a beneficial effect on blood vessels. In addition, some nutritional components have a supporting effect on blood vessel relaxation. Optimum blood vessel relaxation is important for maintaining normal blood pressure, decreased risk of atherosclerosis, maintaining healthy erections and other functions. Therefore, there is an urgent objective to develop effective, economic, and side effects free approaches to help men of all ages to preserve and protect their health.

SUMMARY

In the instant disclosure various combination of micronutrients as a pharmaceutical composition such as Mix 1 and Mix A were used to treat and enhance, testosterone production, testosterone secretion, vascular smooth muscle cell contraction and relaxation functions in normal and inflammatory conditions thus improving men's health. In one embodiment a physiological dose for a mammal was calculated based on daily consumption. The formula was packaged in drug formulation for easy consumption.

In one embodiment, the micronutrient composition comprises or consists of Rosemary extract, Fenugreek, Cassia nomane, 3'3-di indolylmethylene, Zinc, Phosphatidylserine, Vitamin D, Vitamin C, Niacin, Theanine, Aspartic acid, Arginine and Dehydroepiandrosterone (DHEA) and this micronutrient composition in the entire application is mentioned as Mix 1. In one embodiment, the micronutrient composition comprises or consists of Rosemary extract, Fenugreek, Cassia nomane, 3'3-di indolylmethylene, Zinc, Phosphatidylserine, Vitamin D, Vitamin C, Niacin, Theanine, Aspartic acid, and Arginine and this micronutrient composition in the entire application is mentioned as Mix A.

In another embodiment, micronutrient mix comprises of Rosemary extract, Fenugreek, Cassia nomane, 3'3-di indolylmethylene, Zinc, Phosphatidylserine, Vitamin D, Vitamin C, Niacin, Theanine, Aspartic acid and Arginine and is stated in this specification as Mix A.

In one embodiment the micronutrient composition Mix 1 comprises of Rosemary extract at 1 mg-6,000 mg, Fenugreek extract 1 mg-50,000 mg and Fenugreek seed powder at 2 mg-8,000 mg, Cassia nomane seed extract powder 1 mg to 1,000 mg and dry extract 1 mg-300 mg, 3'3-di indolylmethylene 1 mg-800 mg, Zinc 0.1 mg-1,000 mg, Phosphatidylserine 1 mg-1,500 mg, Vitamin D 20 IU-10,000 IU, Vitamin C 10 mg-50,000 mg, Niacin 1 mg-3,000 mg, Theanine 0.1 mg-10,000 mg, Aspartic acid 10 mg-10,000 mg, Arginine 10 mg-50,000 mg and Dehydroepiandrosterone (DHEA) 1 mg-500 mg. In one embodiment the micronutrient composition Mix 1 consists of Rosemary extract at 1 mg-6,000 mg, Fenugreek extract 1 mg-50,000 mg and Fenugreek seed powder at 2 mg-8,000 mg, Cassia nomane seed extract powder 1 mg to 1,000 mg and dry extract 1 mg-300 mg, 3'3-di indolylmethylene 1 mg-800 mg, Zinc 0.1 mg-1,000 mg, Phosphatidylserine 1 mg-1,500 mg, Vitamin D 20 IU-10,000 IU, Vitamin C 10 mg-50,000 mg, Niacin 1 mg-3,000 mg, Theanine 0.1 mg-10,000 mg, Aspartic acid 10 mg-10,000 mg, Arginine 10 mg-50,000 mg and Dehydroepiandrosterone (DHEA) 1 mg-500 mg.

In one embodiment, a micronutrient composition shown as Mix A comprises of Rosemary extract at 1 mg-6,000 mg, Fenugreek extract 1 mg-50,000 mg and Fenugreek seed powder at 2 mg-8,000 mg, Cassia nomane seed extract powder 1 mg to 1,000 mg and dry extract 1 mg-300 mg, 3'3-di indolylmethylene 1 mg-800 mg, Zinc 0.1 mg-1,000 mg, Phosphatidylserine 1 mg-1,500 mg, Vitamin D 20 IU-10,000 IU, Vitamin C 10 mg-50,000 mg, Niacin 1 mg-3,000 mg, Theanine 0.1 mg-10,000 mg, Aspartic acid 10 mg-10,000 mg, and Arginine 10 mg-50,000 mg.

In one embodiment, a micronutrient composition shown as Mix A consists of Rosemary extract at 1 mg-6,000 mg, Fenugreek extract 1 mg-50,000 mg and Fenugreek seed powder at 2 mg-8,000 mg, Cassia nomane seed extract powder 1 mg to 1,000 mg and dry extract 1 mg-300 mg, 3'3-di indolylmethylene 1 mg-800 mg, Zinc 0.1 mg-1,000 mg, Phosphatidylserine 1 mg-1,500 mg, Vitamin D 20 IU-10,000 IU, Vitamin C 10 mg-50,000 mg, Niacin 1 mg-3,000 mg, Theanine 0.1 mg-10,000 mg, Aspartic acid 10 mg-10,000 mg, and Arginine 10 mg-50,000 mg.

In one embodiment, a method of treating a male suffering from a disease due to chronic inflammation, or a side effect such as low testosterone due to diseases such as diabetes, heart disease, cancer and rheumatoid arthritis or advanced age.

In one embodiment, micronutrient composition, the Mix 1 and the Mix A are used as a pharmaceutical composition and administered to a human suffering from reduced testosterone levels induced by specific diseases such as diabetes, cardiovascular disease, and rheumatoid arthritis or advanced age. The micronutrient composition, the Mix A and Mix 1 are administered in various forms to a human to treat male physiological disease such as low testosterone or reduced physiological health due to specific diseases, such as diabetes, cardiovascular disease, and rheumatoid arthritis or resulting from advanced age.

BRIEF DESCRIPTION OF DRAWINGS

Example embodiments are illustrated by way of example and not limitation in the figures of the accompanying drawings, in which like references indicate similar elements and in which:

FIG. 11 shows effects of Mix 1 applied with and without Ascorbic acid on RANTES secretion by Leydig cells under LPS challenge.

Figure 1:
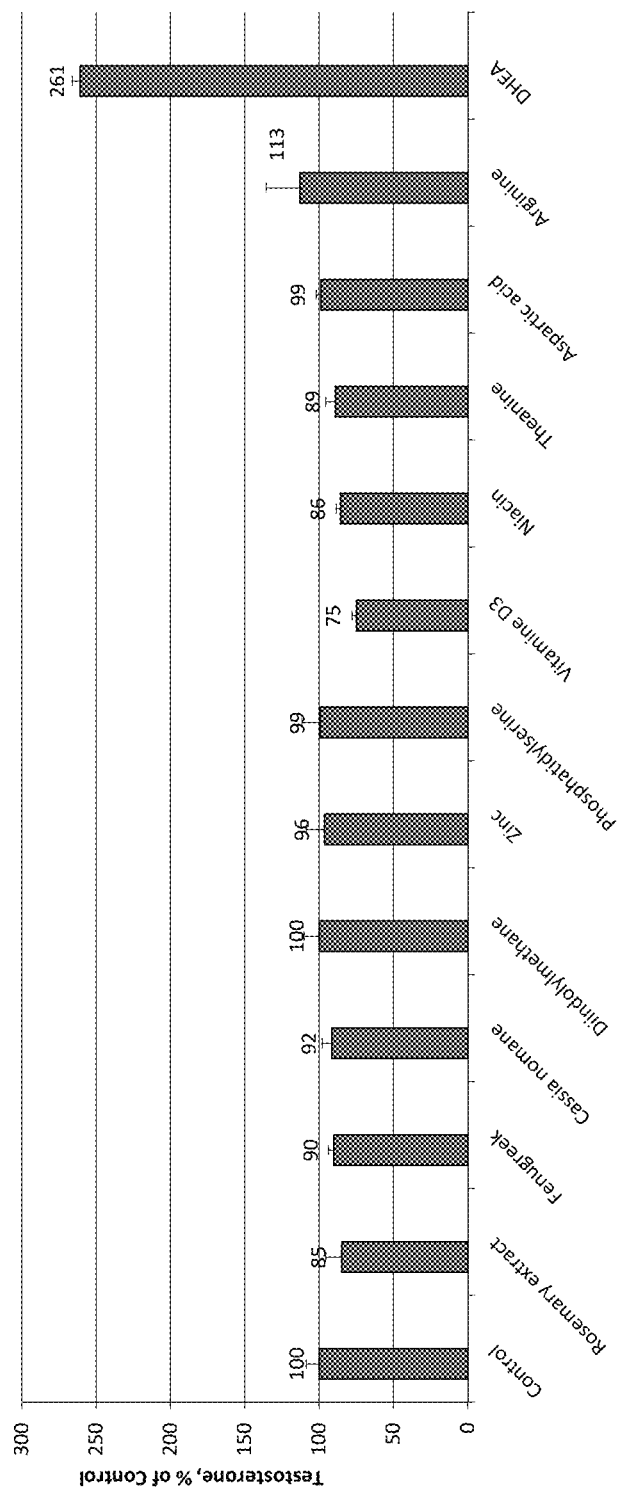
FIG. 1 shows the effects of individual components in micronutrient composition of Mix 1 on testosterone production.

Others features of the present embodiments will be apparent from the accompanying drawings and from the detailed description that follows.

DETAILED DESCRIPTION

The instant disclosure shows various combinations of individual components of micronutrient composition, Mix 1 and Mix A and their effect on preventing and treating low testosterone related functions, are used as a pharmaceutical composition and administered to a human suffering from reduced testosterone levels induced by specific diseases such as diabetes, cardiovascular disease, and rheumatoid arthritis as well as advanced age. The micronutrient composition or pharmaceutical composition as a Mix 1 comprises of Rosemary extract, Fenugreek, Cassia nomane, 3'3-di indolylmethylene, Zinc, Phosphatidylserine, Vitamin D, Vitamin C, Niacin, Theanine, Aspartic acid, Arginine and Dehydroepiandrosterone (DHEA). The physiological range of micronutrient composition for Mix 1 is Rosemary extract at 1-6,000 mg, Fenugreek extract 1-50,000 mg and Fenugreek seed powder at 2-8,000 mg, Cassia nomane seed extract powder 1 to 1,000 mg and dry extract 1 –300 mg, 3'3-di indolylmethylene 1 mg-800 mg, Zinc 0.1-1,000 mg, Phosphatidylserine 1–1,500 mg, Vitamin D 20-10,000 IU, Vitamin C 10-50,000 mg, Niacin 1-3,000 mg, Theanine 0.1-10,000 mg, Aspartic acid 10-10,000 mg, Arginine 10-50,000 mg and Dehydroepiandrosterone (DHEA) 1-500 mg for the physiological range of micronutrient composition for Mix A is Rosemary extract at 1-6,000 mg, Fenugreek extract 1-50,000 mg and Fenugreek seed powder at 2-8,000 mg, Cassia nomane seed extract powder 1 to 1,000 mg and dry extract 1 –300 mg, 3'3-di indolylmethylene 1 mg-800 mg, Zinc 0.1-1,000 mg, Phosphatidylserine 1–1,500 mg, Vitamin D 20-10,000 IU, Vitamin C 10-50,000 mg, Niacin 1-3,000 mg, Theanine 0.1-10,000 mg, Aspartic acid 10-10,000 mg, and Arginine 10-50,000 mg.

Optimum contraction and relaxation of smooth muscle cells is important for the cardiovascular system functions (blood pressure, erectile function) as well as maintaining bronchial air passages (asthma), urogenital systems and other hollow organs. Anti-inflammatory effects of micronutrients in testes cells were investigated to observe effects of individual compounds, Mix 1 and Mix A in human Leydig cells under pro-inflammatory conditions (LPS). Chemokines are a large family of small cytokines with chemo-attractant properties. CCLS chemokine RANTES stands for (Regulated upon Activation, Normal T Cell Expressed and Presumably Secreted) is a pro-inflammatory chemokine, recruiting leukocytes to the site of inflammation. It is chemotactic for T cells, eosinophils, and basophils, monocytes, natural-killer (NK) cells, dendritic cells, and mastocytes. IL-6 plays roles in chronic inflammation—it is a multifunctional cytokine with a wide range of immune and hematopoietic activities and its potent ability to induce the acute phase response.

Effects of individual compounds and the Mix 1 on IL-6 secretion in human aortic endothelial cells were studied to observe anti-Inflammatory effects of micronutrients in vascular cells.

Materials and Methods: This section shows list of all tested ingredients, list of ingredients included in the new formulation, Testosterone production by mouse Leyden TM3 cells, Collagen gel contraction by AoSMC, Cytokines production by mouse Leyden TM3 cells. Cytokine panel, Cytokines production by AoEC: IL6, IL2, TNFa, ATP production by rat myocyte H9C2 cells and SIRT1 expression in mouse Leyden TM3 cells.

TABLE 1

List of Ingredients and their suppliers.

| NN | Ingredient | Supplier | Stock Solution Solvent | Stock Solution Concentration, mg/ml |
|---|---|---|---|---|
| 1 | Rosemary extract | BulkSupplements.com | DMSO | 100 |
| 2 | Horny Goat weed | BulkSupplements.com | DMSO | 100 |
| 3 | Ginseng Root Extract | BulkSupplements.com | DMSO | 100 |
| 4 | Fenugreek Powder | BulkSupplements.com | DMSO | 100 |

TABLE 1-continued

List of Ingredients and their suppliers.

| NN | Ingredient | Supplier | Stock Solution Solvent | Stock Solution Concentration, mg/ml |
|---|---|---|---|---|
| 5 | Safed Musli Powder | MB Herbals | DMSO | 100 |
| 6 | Cassia nomane, Cassia-20:1 Natural Bark Extract Powder | Prescribed for Life | DMSO | 100 |
| 7 | Resveratrol Powder | BulkSupplements.com | DMSO | 100 |
| 8 | Lycopene | BulkSupplements.com | DMSO | 100 |
| 9 | Diindolylmethane (DIM) | BulkSupplements.com | DMSO | 100 |
| 10 | Zinc Acetate Dihydrate | Sigma-Aldrich | Water | 10 |
| 11 | Boric Acid | Sigma-Aldrich | Water | 10 |
| 12 | Phosphatidylserine | BulkSupplements.com | Ethanol/Chloroform (50%/50%) | 100 |
| 13 | Cholecalciferol Vitamin D3 | Sigma-Aldrich | Ethanol | 100 |
| 14 | Piperine from Black pepper extract | Sigma-Aldrich | DMSO | 100 |
| 15 | Niacin | Powder | Water | 10 |
| 16 | L-Theanine | Microingredients | Water | 10 |
| 17 | Ashwaganda Extract | BulkSupplements.com | DMSO | 100 |
| 18 | Aspartic acid | Sigma-Aldrich | Water | 10 |
| 19 | L-Arginine | Sigma-Aldrich | Water | 10 |
| 20 | Tribulus Terrestris Extract | BulkSupplements.com | DMSO | 100 |
| 21 | Shilajit Powder, 50% Fulvic Acid | Matcha Outlet | DMSO | 100 |
| 22 | Longjack | BulkSupplements.com | DMSO | 100 |
| 23 | Dehydroepiandrosterone (DHEA) | Sigma-Aldrich | Water | 10 |
| 24 | L-Ascorbic Acid | Sigma-Aldrich | Water | 10 |
| 25 | L-Citrulin | Sigma-Aldrich | Water | 10 |

Stock solutions of ingredients were prepared by dissolution in corresponding solvent followed by filtration through 0.2 microm sterile filter. Stock solutions were appropriately aliquoted and stored at −20° C. until use in experiments.

TABLE 2

List of ingredients included in the new formulation Mix 1.

| NN | Ingredient | Final Tested Concentration, mcg/ml |
|---|---|---|
| 1 | Rosemary extract | 20 |
| 2 | Fenugreek | 20 |
| 3 | Cassia nomane | 20 |
| 4 | 3,3-di indolylmethylene (Diindolylmethane) | 5 |
| 5 | Zinc | 2 |
| 6 | Phosphatidylserine | 20 |
| 7 | Vitamine D3 | 5 |
| 8 | Niacin | 20 |
| 9 | Theanine | 2 |
| 10 | Aspartic acid | 2 |
| 11 | Arginine | 2 |
| 12 | DHEA | 2 |

TABLE 3

List of ingredients included in the new formulation Mix A.

| NN | Ingredient | Final Tested Concentration, mcg/ml |
|---|---|---|
| 1 | Rosemary extract | 20 |
| 2 | Fenugreek | 20 |
| 3 | Cassia nomane | 20 |
| 4 | 3,3-di indolylmethylene (Diindolylmethane) | 5 |
| 5 | Zinc | 2 |
| 6 | Phosphatidylserine | 20 |
| 7 | Vitamine D3 | 5 |
| 8 | Niacin | 20 |
| 9 | Theanine | 2 |
| 10 | Aspartic acid | 2 |
| 11 | Arginine | 2 |

Testosterone production assay: Mouse Leyden TM3 cells (ATCC) were cultured at 37° C., 5% CO2, in growth medium: 1:1 mixture of Ham's F12 medium and Dulbecco's modified Eagle's medium with 2.5 mM L-Glutamine, 0.5 mM Sodium Pyruvate, 1.2 g/L Sodium Bicarbonate and 15 mM HEPES, 92.5%; horse serum, 5%; fetal bovine serum, 2.5%. TM3 cells were seeded in 96-well plates covered with fibronectin or collagen (COSTAR) in 100 and/well growth medium. After reaching confluency cells were supplied with tested components in 100 mcl growth medium for 48 hour incubation. In some tests we also used additions of TNF alpha at 1 ng/ml and 10 ng/ml as indicated in appropriate figure legends. Testosterone content in 50 mcl conditioned cell culture medium samples was assayed with testosterone ELISA assay (DRG #EIA-1559) as described in the manufacturer's protocol.

Collagen gel contraction by AoSMC: Gel Contraction Assay: Human aortic smooth muscle cells (AoSMS) were obtained from Lonza Corporation and cultured in DMEM cell culture medium (ATCC) supplemented with 5% fetal bovine serum (ATCC). For experiments cells were suspended in DMEM medium at 500,000 per mL by trypsinization and mixed with equal volume of 2 mg/ml bovine skin collagen (Sigma) solution in DMEM. Resulting cell suspension was distributed at 300 mcl per well of plastic 24 well plate pretreated with 10 mg/ml bovine serum albumin in phosphate buffered saline. Collagen gels, formed in the wells after one hour incubation at 37° C., were supplemented with 500 mcl DMEM containing indicated amounts of tested compounds. After 24 hours incubation at 37° C. pictures of the wells were taken with digital photo camera and gel surface area was measured in pixels using ImageJ scientific software. Gel contraction was expressed as percentage of unsupplemented control using the following formula: (No Cell Control Gel Area–Tested Sample Gel Area)/(No Cell Control Gel Area–Not Supplemented Control Gel Area)*100%. All experiments were done in triplicates and results are expressed as mean values+/–SD.

Cytokine Assays in TM3 cells: TM3 cells cultured in 96 well plates were supplemented with tested compounds in the presence of 10 ng/ml liposaccharide (LPS, Sigma) as described above. Levels of IGF1 and RANTES were assayed with corresponding ELISA assays (R&D Systems). In separate experiment TM3 cells were grown in 6 well plates and supplemented or not with 10 ng/ml LPS in the presence of test compounds. Conditioned cell culture medium was subjected for mouse 24 or 36 cytokine array assay (Signosis) according to the manufacturer's protocol.

Cytokine assay in Human Aortic endothelial cells (AoEC): Human Aortic endothelial cells (AoEC, Lonza) were cultured in EBG-2 cell culture medium (Lonza) and used in experiments at 5-8 passages. AoEC were seeded in 96-well plates covered with fibronectin or collagen (COSTAR) in 100 mcl/well growth medium. After reaching confluency cells were supplemented with tested components in 100 mcl growth medium for 48 hour incubation. Levels of cytokines were assayed with corresponding ELISA assays (R&D Systems).

ATP production in myocyte H9C2 cells: Rat myocyte H9C2 cells (ATCC) were cultured in 10% FBS/DMEM cell growth medium. H9C2 cells cultured in 96 well plates were subjected to treatments with tested compounds for 48 hours at 37° C. Levels of adenosine triphosphate (ATP) were assayed by Promega CellTiter GLO Luminescent Cell Viability Assay G7572 according to the manufacturer's protocol.

SIRT1 expression in mouse Leyden TM3 cells: TM3 cells were supplemented with tested compounds in growth medium in 96 well plates as described above. SIRT1 levels in conditioned cell culture medium were determined with Elabscience Mouse SIRT1 (Sirtuin) ELISA Kit #E-EL-M0350 according to the manufacturer's protocol.

FIG. 1 shows the effects of individual components present in the micronutrient composition of Mix 1 on testosterone production in TM3 cells. The results show testosterone secretion evaluated under normal conditions and they indicate low efficacy of individual compounds, except when DHEA on testosterone secretion. DHEA applied individually increased testosterone secretion by 161% compared to control. The concentration of ingredients were Rosemary extract 20 mcg/ml, Fenugreek-20 mcg/ml, Cassia nomane—20 mcg/ml, 3'3-di indolylmethylene—5 mcg/ml, Zinc—2 mcg/ml, Phosphatidylserine—20 mcg/ml, Vitamin D—5 mcg/ml, Niacin—20 mcg/ml, Theanine—2 mcg/ml, Aspartic acid—2 mcg/ml, Arginine—2 mcg/ml and DHEA—2 mcg/ml.

Figure 2:
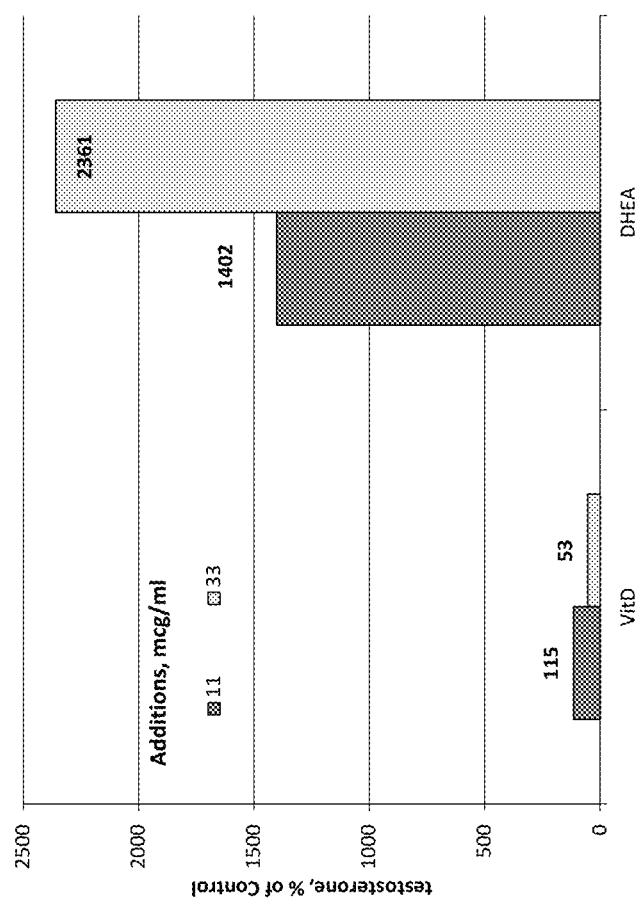
FIG. 2 shows the effects of Vitamin D3 and DHEA on testosterone production by TM3 cells.

FIG. 2 results show Testosterone secretion by TM3 cells under normal conditions comparing the effects of DHEA and vitamin D3. DHEA was much more effective than vitamin D in promoting testosterone secretion. At DHEA concentrations of 11 and 33 mcg/ml the secretion of testosterone increased by 1402% and 2361% respectively, compared to control. This DHEA effect was several fold higher than obtained in the presence of vitamin D3, i.e. at 11 mcg/ml concentration the testosterone secretion in the presence of DHEA was it was 1402% and in the presence of Vitamin D—115% of Control.

Figure 3:
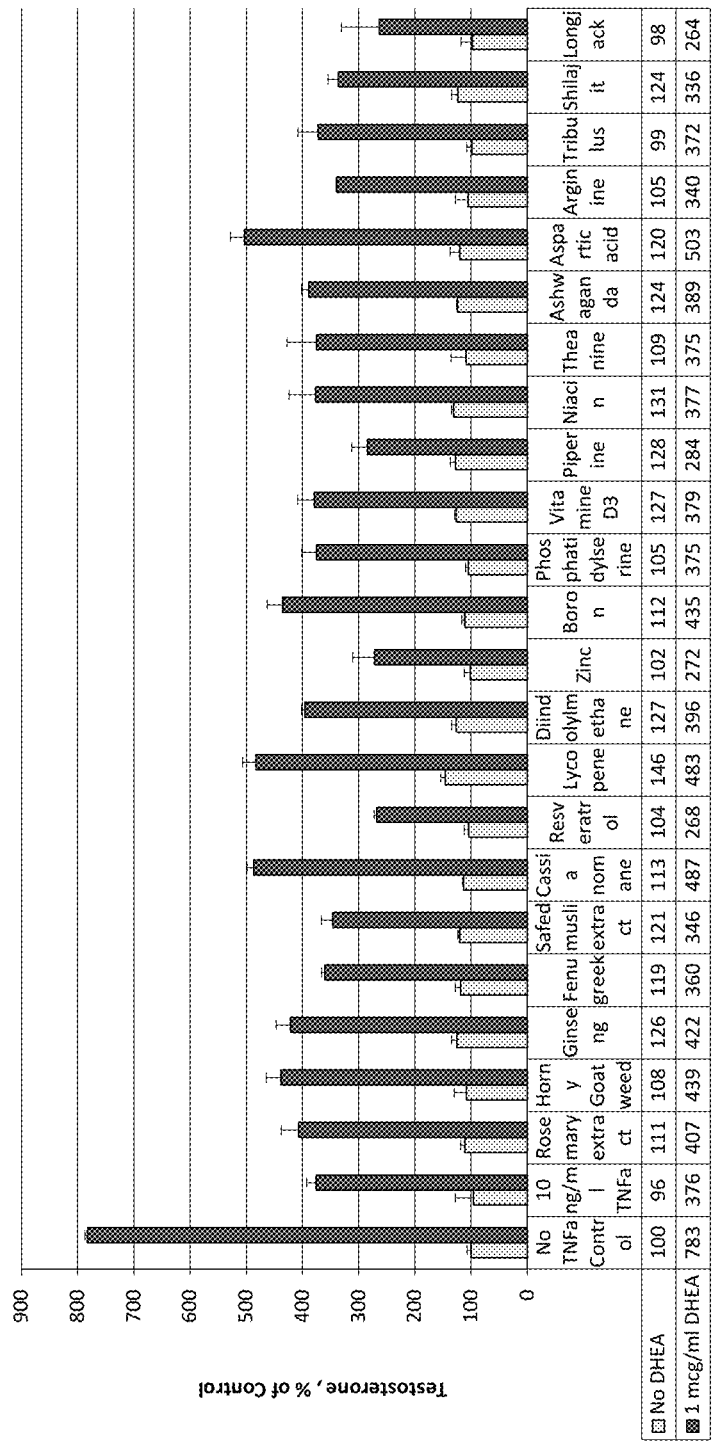
FIG. 3 shows the effects of individual natural compounds applied with and without DHEA on testosterone secretion under pro-inflammatory conditions.

FIG. 3 shows Testosterone secretion under pro-inflammatory conditions and effects of individual compounds and Mix 1. It is known that chronic inflammation, such as in the presence of TNF alpha, can suppress testosterone production, which has physiological implications as it is related to an increased risk of infertility. Incubation was for 48 h with 10 ng/ml TNFa (all samples) and 1 mcg/ml DHEA or w/o DHEA. Data are presented as % of no additions Control. We evaluated the effects of micronutrients on testosterone production in Leydig cells exposed to a proinflammatory factor—TNF alpha.

The results show that under inflammatory condition (TNF alpha present) the DHEA can significantly decrease testosterone secretion by TM3 cells compared to normal Control (decrease by about 48%). Other individual compounds evaluated in the presence and absence of DHEA have either decreasing (ie resveratrol, zinc) or stimulatory effect on testosterone secretion. As such, under pro-inflammatory conditions the combination of DHEA with Aspartic acid, Cassia nomane extract and lycopene had the most pronounced effects by increasing testosterone secretion by 34%, 30% and 29% respectively, compared to control (with TNF alpha).

Figure 4:
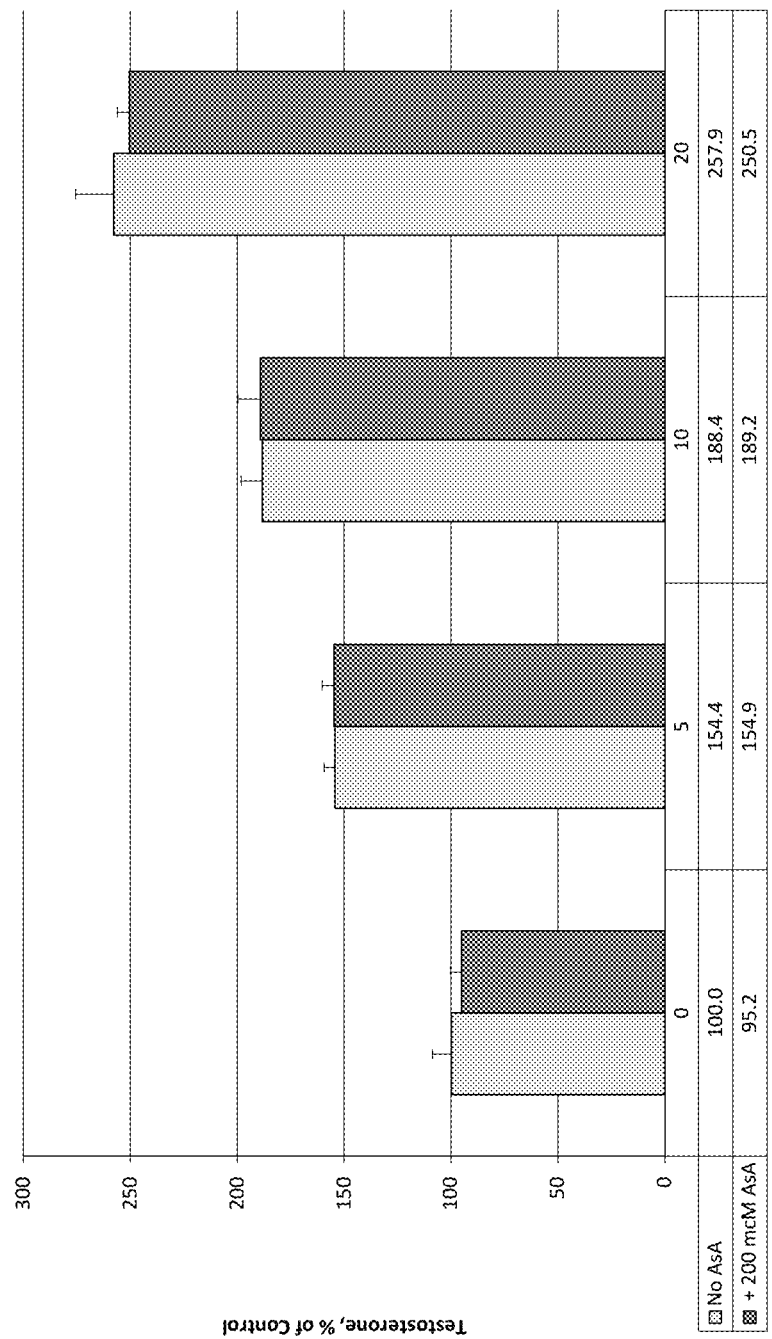
FIG. 4 shows Testosterone secretion under pro-inflammatory conditions and effects of different concentrations of Mix 1 applied with and without Ascorbic acid.

FIG. 4 shows dose-dependent effects of Mix 1 (all components) on Testosterone production in TM3 cells. The results indicate concentration dependent stimulatory effects of Mix 1 on testosterone secretion by Leydig cells in the presence of TNF alpha (1 ng/m). In the presence of Mix 1 at 20 mcg/ml, the testosterone secretion increased by 158% compared to Control. Addition of 200 mcM Ascorbate to Mix 1 did not have any additional effect on testosterone production under this condition.

Figure 5B:
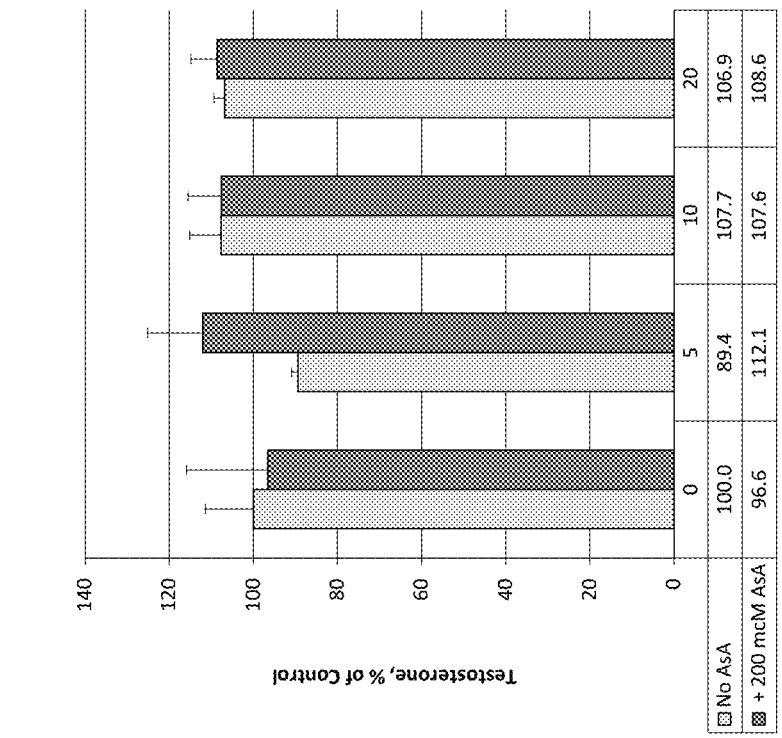
FIG. 5A shows dose-dependent effects of Mixture Q (w/o DHEA, DIM, Casia) applied with and without Ascorbic acid on Testosterone production in TM3 cells.
FIG. 5 B shows dose-dependent effects of Mixture A (w/o DHEA) applied with and without Ascorbic acid on Testosterone production in TM3 cells.
Figure 5A:
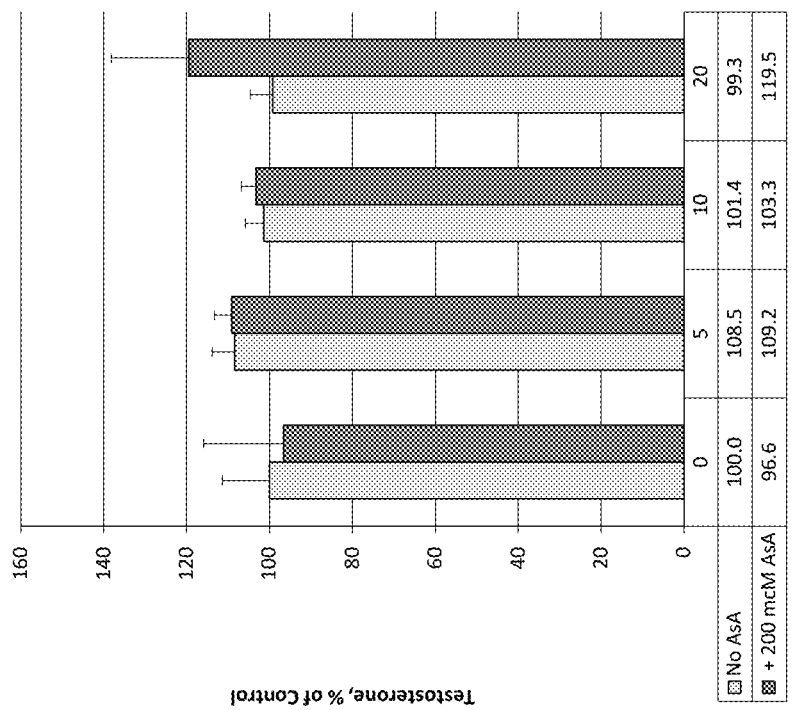

FIG. 5A shows dose-dependent effects of Mixture Q (w/o DHEA, DIM, Casia) on Testosterone production in TM3 cells. FIG. 5 B shows dose-dependent effects of Mix A (w/o DHEA) on Testosterone production in TM3 cells. The results presented in FIG. 5A and FIG. 5B illustrate the importance of some ingredients contained in Mix 1 on testosterone secretion. Without DHEA, DIM and Cassia extract the remaining ingredients in the Mix 1 or Mix A did not have any impact on testosterone production in Leydig cells in the presence TNF alpha (1 ng/ml). It appears that the critical ingredient is DHEA.

Figure 6:
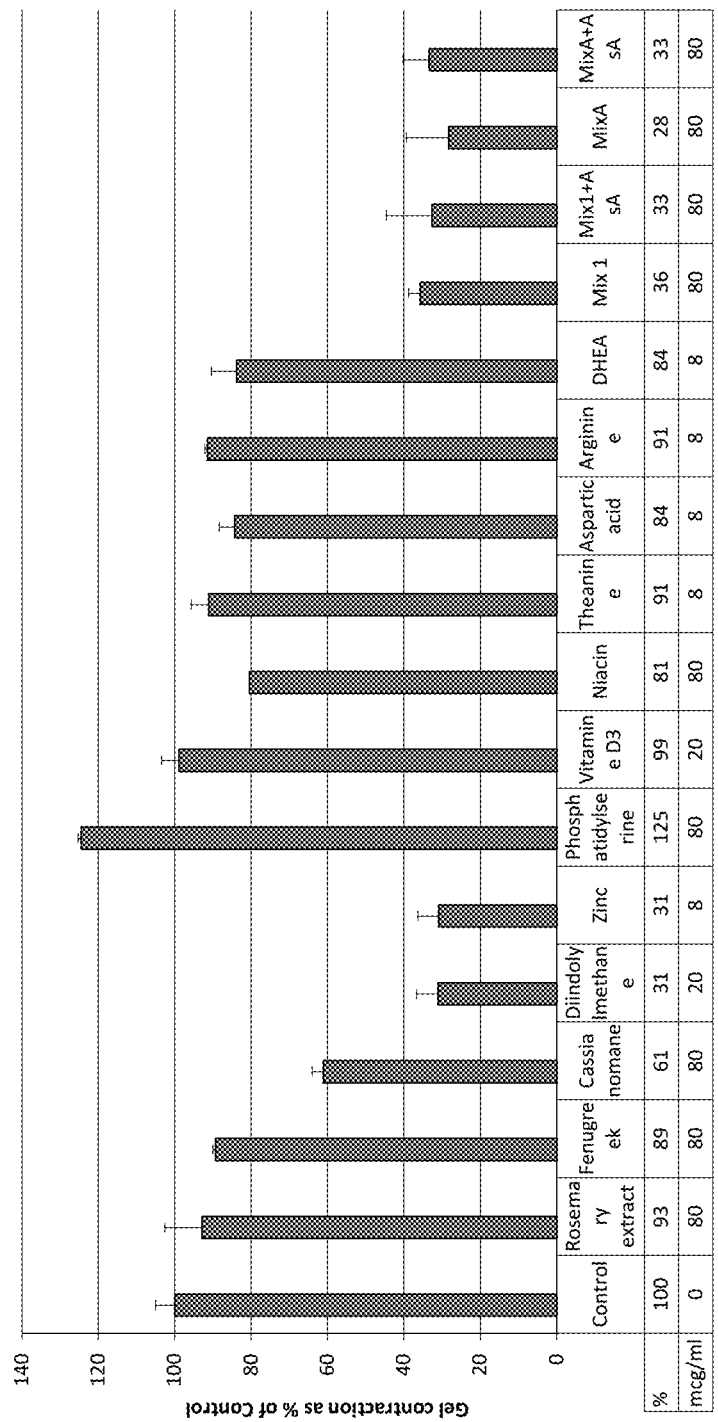
FIG. 6 shows effects of individual components and their combinations in Mix 1 and MixA on Gel Contraction by AoSMC. Combinations were used at 80 mcg/ml arbitrary concentration.

FIG. 6 shows smooth muscle (SMC) driven gel contraction and effects of individual compounds, the Mix 1 and Mix A. The results show that Mix 1 and Mix A have relaxing effects on smooth muscle cells driven gel contraction. SMC contraction decreased by 64% (Mix1) and 72% (Mix A). The addition of ascorbate 200 mcg to Mix 1 had an additional but non-significant relaxing effect (up to 66%). This level of relaxation was also achieved in the presence of Mix A and ascorbate. Among individual compounds the most effective ones in achieving SMC relaxation were Di-indolylmethane and zinc, both of which promoted SMC relaxation by 69%.

Figures 7A, 7B:
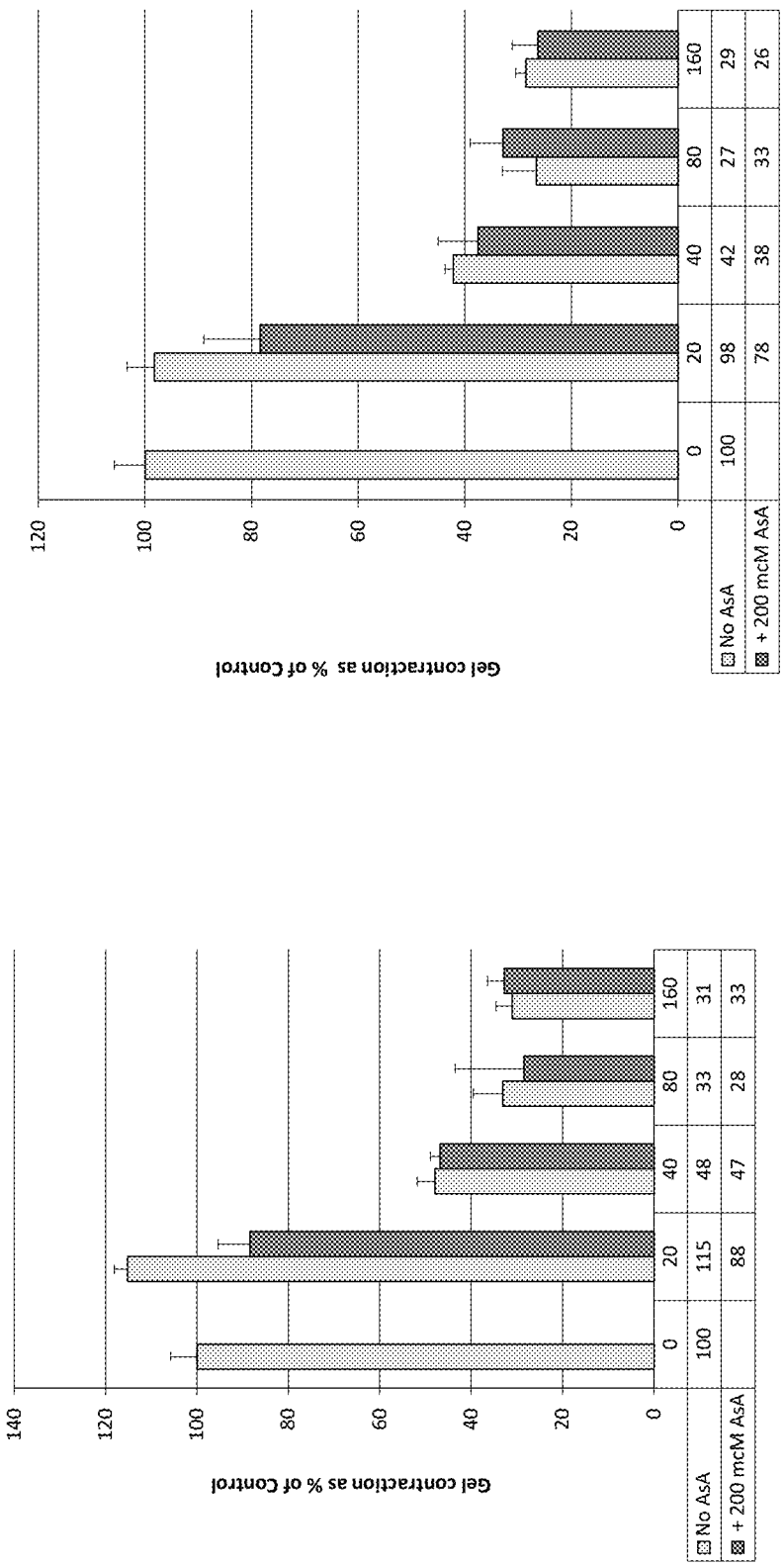
FIG. 7A and FIG. 7B shows effects of Mix 1 and Mix A (w/o DHEA) on SMC driven gel contraction.

In FIG. 7A and FIG. 7B the results show concentration dependent effects of Mix 1 and Mix A (without DHEA) on smooth muscle cells driven gel contraction. Both mixtures applied at 160 mcg/ml showed similar SMC-driven relaxing effects with 69% relaxation in the presence of Mix 1 and 71% with Mix A (w/o DHEA). Addition of ascorbate further increased relaxation effects only when the mixes were used at a low concentration of 20 mcg/ml.

Figure 8:
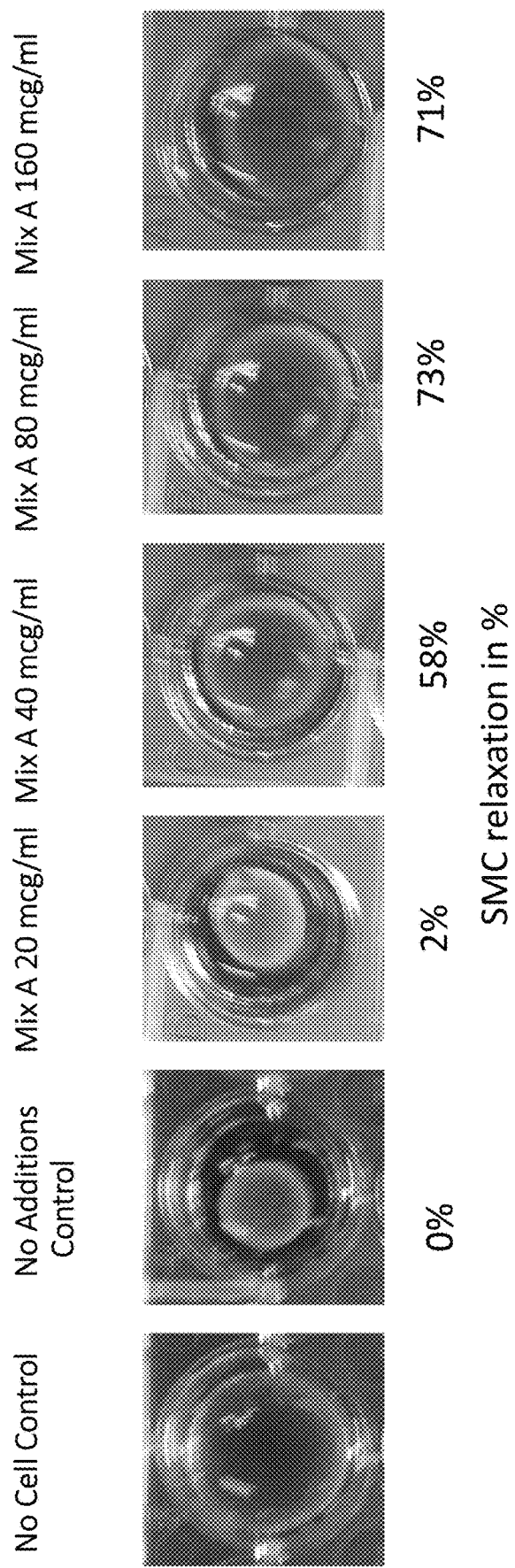
FIG. 8 shows representative images of collagen gel contraction driven by AoSMC under treatment with different concentrations of Mix A.

FIG. 8 shows representative images of collagen gel contraction by AoSMC under treatment with Mix A.

Figure 9:
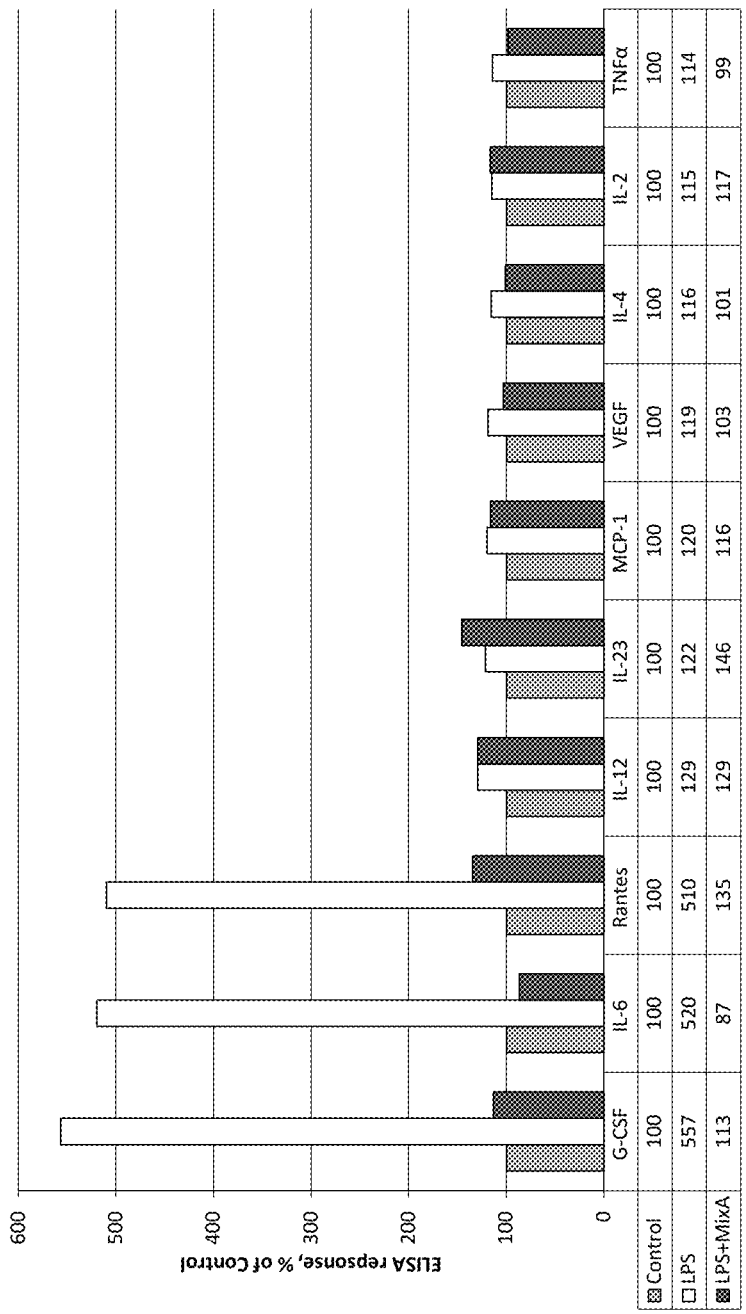
FIG. 9 shows changes in the cytokines profile in the presence of Mix A (w/o DHEA) in Leydig cells under pro-inflammatory conditions.

FIG. 9 shows changes in the cytokines profile in the presence of Mix A (w/o DHEA) in Leydig cells under pro-inflammatory conditions. Cytokine expression was evaluated in murine Leydig cells (line TM3) treated with 10 ng/ml LPS and 20 mcg/ml Mix A (No DHEA) for 2 days. Ten Highest Responders to LPS in general were tested. The results show that in the presence of LPS the Leydig cells increased the secretion of 11-6, G-CFS and Rantes by over 5-fold, compared to controls. The secretion of other cytokines was only slightly affected (by up to 29%). The addition of Mix A in the presence of LPS had significant lowering effects on secretion of G-CSF, IL-6 and RANTES by decreasing these cytokines to the control (non-inflammatory) levels. FIG. 9 shows changes in the cytokines profile in the presence of Mix A (w/o DHEA) in Leydig cells under pro-inflammatory conditions.

Figure 10:
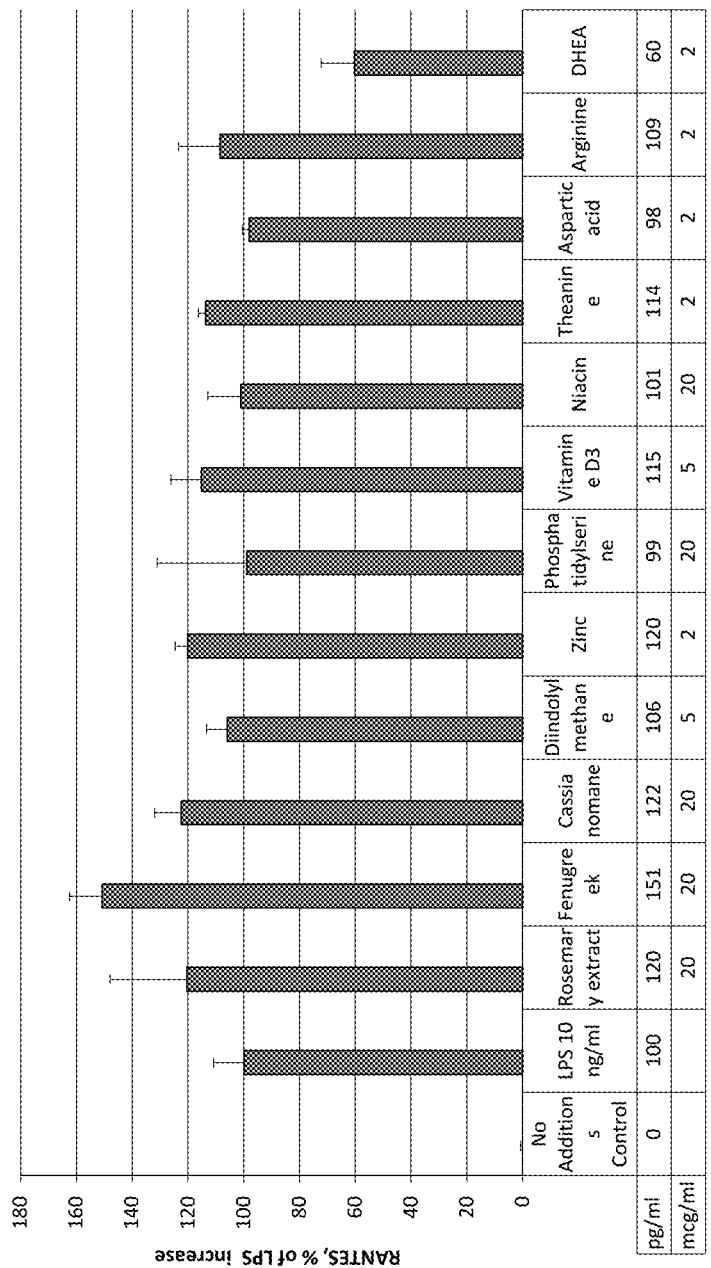
FIG. 10 shows the effects of individual ingredients in Mix 1 on RANTES secretion by Leydig cells under LPS challenge.

FIG. 10 shows effects of individual components on RANTES production by TM3 Leydig cells under 10 ng/ml LPS challenge. Individual components concentrations correspond to Mix 1 and Mix A at 20 mcg/ml level and results are shown as % of LPS-dependent increase. The results show the effects of individual compounds on RANTES secretion in Leydig cells exposed to LPS. Some test ingredients (i.e. Fenugreek, rosemary extract, Cassia nomane) increased RANTES secretion. Only DHEA showed significant-40%-decrease in RANTES. This result signifies importance of nutrient interactions in achieving final effect of the mixture.

Figure 11:
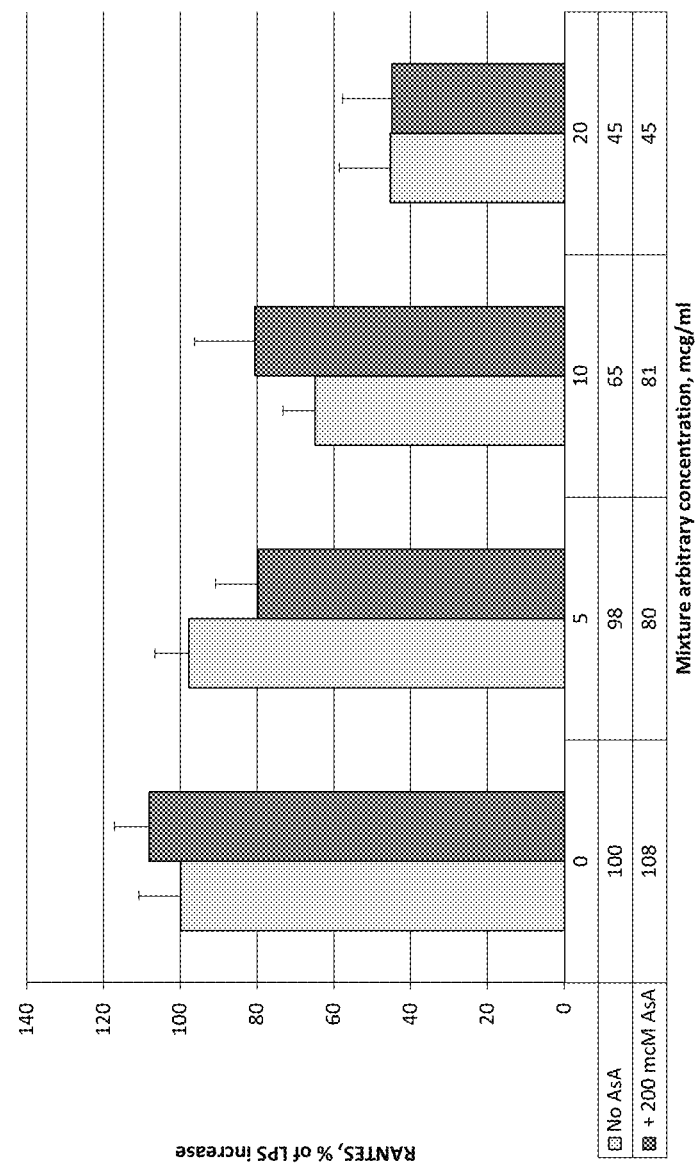
FIG. 11 shows

FIG. 11 shows effects of Mix 1 on RANTES secretion by Leydig cells under LPS challenge. Dose-dependent effects of Mix 1 (all components) on RANTES secretion in TM3 Leydig cells was evaluated in the presence of 10 ng/ml LPS. Results are shown as % of LPS-dependent increase. In contrast to the effects some of the individual compounds on RANTES in Leydig cells exposed to LPS (previous slide) their combination in Mix 1 resulted in a significant, concentration dependent inhibitory effect on RANTES by 55%. Ascorbate combined with Mix 1 at its low (5 mcg/ml) concentration enhanced the inhibitory effect of Mix 1 on RANTES from 2% to 20%. However, ascorbate did not have any additional effect on RANTES when combined with higher concentration of Mix 1 (20 mcg/ml).

Figure 12:
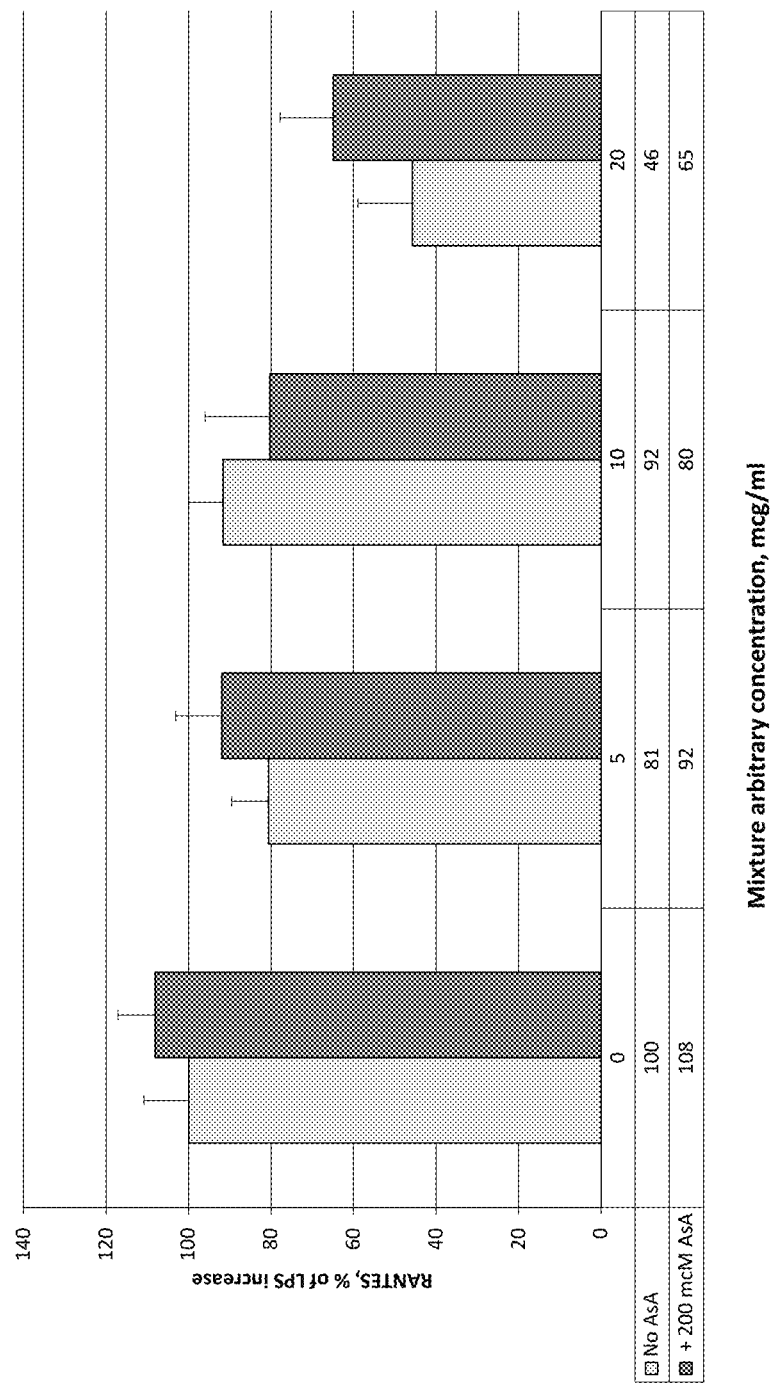
FIG. 12 shows effects of Mix A (w/o DHEA) applied with and without Ascorbic acid on RANTES secretion by Leydig cells under LPS challenge.

FIG. 12 shows dose-dependent effects of Mix A (w/o DHEA) on RANTES secretion by TM3 Leydig cells in the presence of 10 ng/ml LPS. Results are shown as % of LPS-dependent increase. The results show concentration dependent inhibitory effects of Mix A on RANTES secretion in Leydig cells exposed to LPS. Mix A applied at 20 mcg/ml concentration inhibited RANTES by 54%. Ascorbate combined with Mix A displayed slightly increasing effects on RANTES, which would suggest an important role of DHEA for anti-inflammatory effect.

Figure 13:
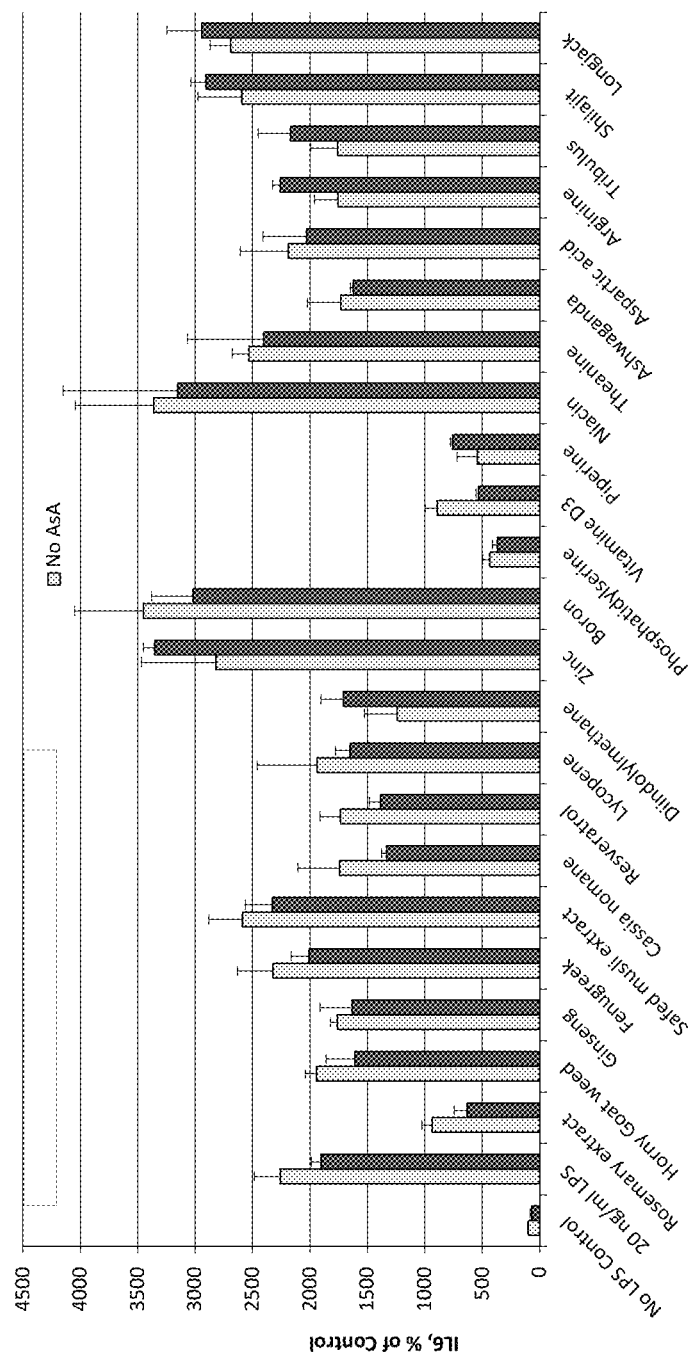
FIG. 13 shows the effects of individual ingredients applied with and without Ascorbic acid on IL6 secretion by human aortic endothelial cells (HAEC) in the presence of LPS.

FIG. 13 shows effects of nutrient candidates for Testosterone mix on IL6 release by Human Aortic Endothelial Cells (HAEC). The test was carried out by incubating HAEC cells for 24 h in the presence of 20 ng/ml LPS (all samples) and 200 mcM Ascorbate or w/o Ascorbate. Data expressed as % of no additions Control is shown in the figure. The results indicate that among individual compounds tested only rosemary, vitamin D, piperine, phosphatidylserine had significant inhibitory effect on 11-6 secretion in HAEC cells exposed to LPS.

Figure 14:
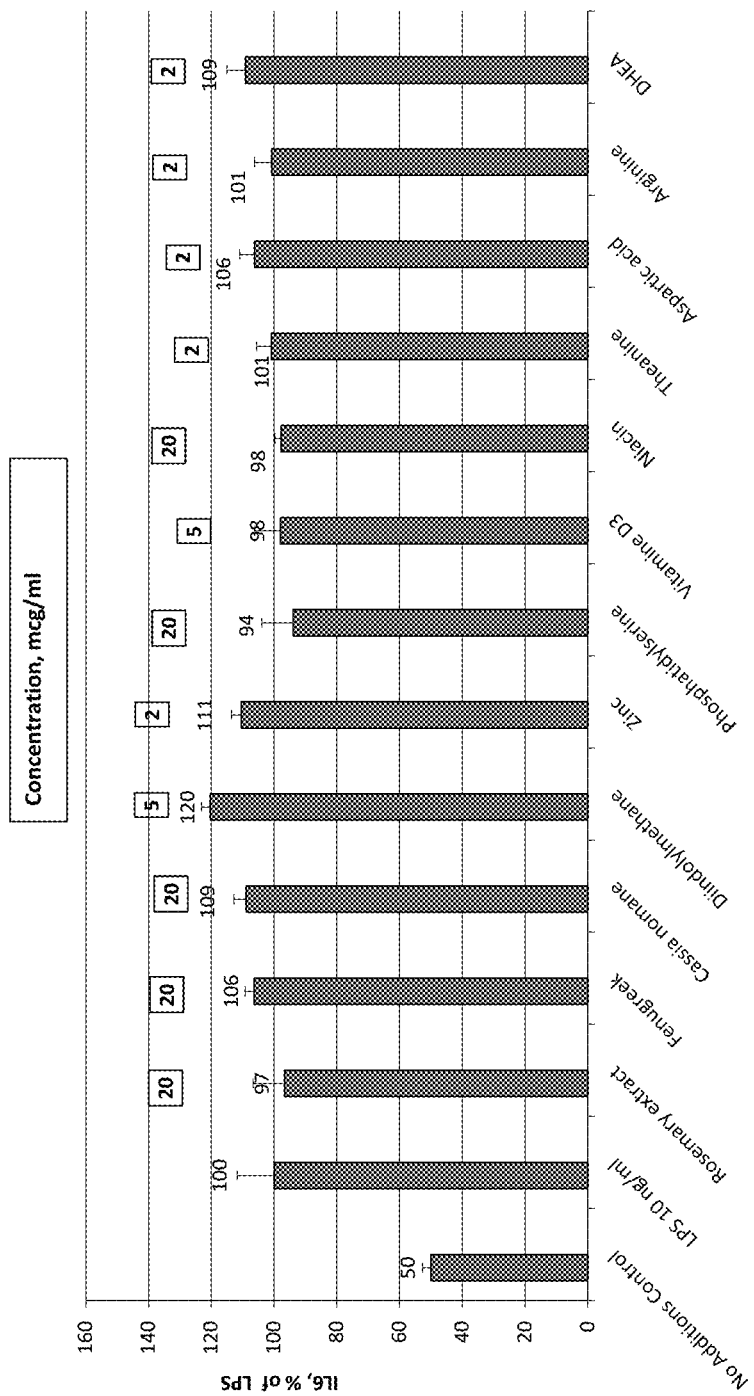
FIG. 14 shows effects of individual ingredients present in the Mix 1 on IL6 secretion by HAEC in the presence of LPS.

FIG. 14 shows effects of individual components on IL-6 production by HAEC. Individual components concentrations correspond to Mix 1 and Mix A at 20 mcg/ml level. The results show that none of the individual compounds present in Mix 1 had significant inhibitory effect on 11-6 secretion in HAEC cells exposed to LPS.

Figure 15:
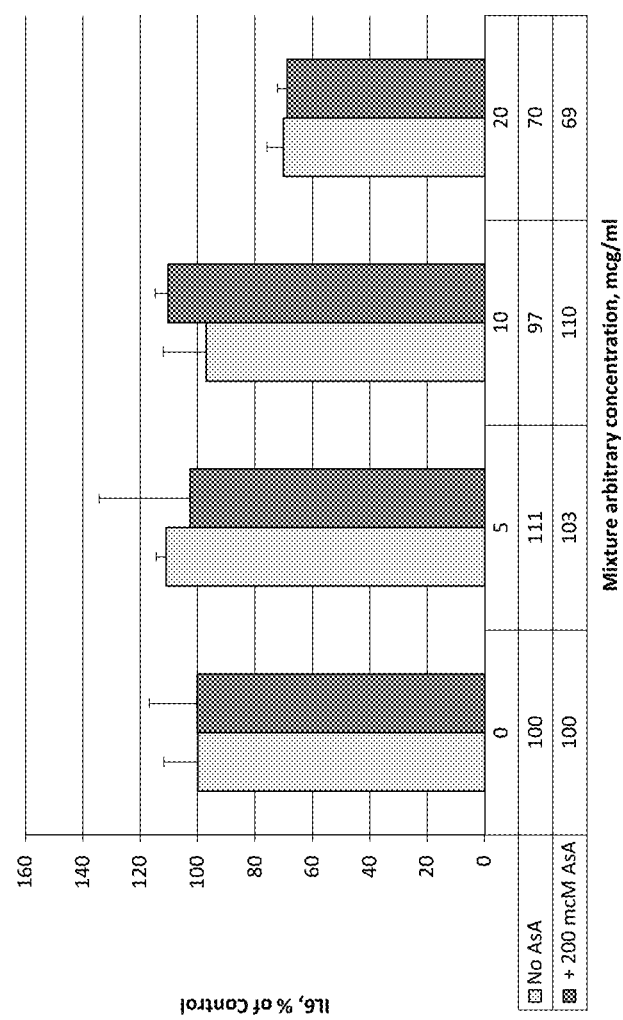
FIG. 15 shows that interaction of ingredients combined in Mix 1 inhibits IL-6 secretion in HAEC.

FIG. 15 shows dose-dependent effects of Mix 1 (all components) on IL6 production in HAEC. The results show that contrary to individual effects, the combined effects of nutrients (Mix 1) results in significant inhibition of 11-6 secretion in HAEC cells exposed to LPS. The effect is concentration dependent with 30% inhibition of IL6 by Mix 1 at 20 mcg/ml. This indicates the significance of nutrients interaction in the mixture.

Drug formulations suitable for these administration routes can be produced by adding one or more pharmacologically acceptable carriers to the agent and then treating the micronutrient composition through a routine process known to those skilled in the art. The mode of administration includes, but is not limited to, non-invasive peroral, topical (for example, transdermal), enteral, transmucosal, targeted delivery, sustained-release delivery, delayed release, pulsed release and parenteral methods. Peroral administration may be administered both in liquid and dry state. In one embodiment, micronutrient composition would be more specifically Mix 1 and Mix A. Mix 1 comprises Rosemary extract at 1 mg-6,000 mg, Fenugreek extract 1 mg-50,000 mg and Fenugreek seed powder at 2 mg-8,000 mg, Cassia nomane seed extract powder 1 mg to 1,000 mg and dry extract 1 mg-300 mg, 3'3-di indolylmethylene 1 mg-800 mg, Zinc 0.1 mg-1,000 mg, Phosphatidylserine 1 mg-1,500 mg, Vitamin D 20 IU— 10,000 IU, Vitamin C 10 mg-50,000 mg, Niacin 1 mg-3,000 mg, Theanine 0.1 mg-10,000 mg, Aspartic acid 10 mg-10,000 mg, Arginine 10 mg-50,000 mg and Dehydroepiandrosterone (DHEA) 1 mg-500 mg and Mix A Rosemary extract at 1 mg-6,000 mg, Fenugreek extract 1 mg-50,000 mg and Fenugreek seed powder at 2 mg-8,000 mg, Cassia nomane seed extract powder 1 mg to 1,000 mg and dry extract 1 mg-300 mg, 3'3-di indolylmethylene 1 mg-800 mg, Zinc 0.1 mg-1,000 mg, Phosphatidylserine 1 mg-1,500 mg, Vitamin D 20 IU-10,000 IU, Vitamin C 10 mg-50,000 mg, Niacin 1 mg-3,000 mg, Theanine 0.1 mg-10,000 mg, Aspartic acid 10 mg-10,000 mg, and Arginine 10 mg-50,000 mg is used as a nutritional supplement composition or as a pharmaceutical composition. There is a process for producing the micronutrient composition Mix 1 and Mix A comprising the steps of mixing the ingredients of the micronutrient composition and optionally formulating the micronutrient composition.

Formulations suitable for oral administration may be in the form of capsules, cachets, pills, tablets, lozenges (using flavored bases, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin or sucrose and acacia), each containing a predetermined amount of a subject composition as an active ingredient. Subject compositions may also be administered as a bolus, electuary or paste.

When an oral solid drug product is prepared, micronutrient composition is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder or capsules. Additives may be those generally employed in the art. Examples of excipients include lactate, sucrose, sodium chloride, glucose, starch, calcium carbonate, kaolin, microcrystalline cellulose and silicic acid. Binders include water, ethanol, propanol, simple syrup, glucose solution, starch solution, liquefied gelatin, carboxymethylcellulose, hydroxypropyl cellulose, hydroxypropyl starch, methyl cellulose, ethyl cellulose, shellac, calcium phosphate and polyvinyl pyrrolidone. Disintegrants include dried starch, sodium arginate, powdered agar, sodium hydroxy carbonate, calcium carbonate, sodium lauryl sulfate, monoglyceryl stearate and lactose. Lubricants include purified talc, stearic acid salts, borax and polyethylene glycol. Sweetening agents include sucrose, orange peel, citric acid and tartaric acid.

When a liquid drug product for oral administration is prepared, micronutrient composition is mixed with an additive such as a sweetening agent, a buffer, a stabilizer, or a flavoring agent, and the resultant mixture is processed through a routine method, to produce an orally administered liquid drug product such as an internal solution medicine, syrup or elixir. Examples of the sweetening agent include vanillin; examples of the buffer include sodium citrate; and examples of the stabilizer include tragacanth, acacia, and gelatin.

For the purposes of transdermal (e.g., topical) administration, dilute sterile, aqueous or partially aqueous solutions (usually in about 0.1% to 5% concentration), otherwise similar to the above parenteral solutions, may be prepared with micronutrient composition.

Formulations containing micronutrient composition for rectal or vaginal administration may be presented as a suppository, which may be prepared by mixing a subject composition with one or more suitable non-irritating carriers, comprising, for example, cocoa butter, polyethylene glycol, a suppository wax or a salicylate, which is solid at room temperature, but liquid at body temperature and, therefore, will melt in the appropriate body cavity and release the encapsulated compound(s) and composition(s). Formulations that are suitable for vaginal administration also include pessaries, tampons, creams, gels, pastes, foams or spray formulations containing such carriers as are known in the art to be appropriate.

A targeted-release portion for capsules containing micronutrient composition can be added to the extended-release system by means of either applying an immediate-release layer on top of the extended release core; using coating or compression processes, or in a multiple-unit system such as a capsule containing extended- and immediate-release beads.

When used with respect to a micronutrient composition, the term "sustained release" is art recognized. For example, a therapeutic composition that releases a substance over time may exhibit sustained-release characteristics, in contrast to a bolus type administration in which the entire amount of the substance is made biologically available at one time. In particular embodiments, upon contact with body fluids, including blood, spinal fluid, mucus secretions, lymph or the like, one or more of the pharmaceutically acceptable excipients may undergo gradual or delayed degradation (e.g., through hydrolysis), with concomitant release of any material incorporated therein, e.g., a therapeutic and/or biologically active salt and/or composition, for a sustained or extended period (as compared with the release from a bolus). This release may result in prolonged delivery of therapeutically effective amounts of any of the therapeutic agents disclosed herein.

Current efforts in the area of drug delivery include the development of targeted delivery, in which the drug is only active in the target area of the body (for example, mucous membranes such as in the nasal cavity), and sustained-release formulations, in which the micronutrient composition is released over a period of time in a controlled manner from a formulation. Types of sustained release formulations include liposomes, drug-loaded biodegradable microspheres and micronutrient composition polymer conjugates.

Delayed-release dosage formulations are created by coating a solid dosage form with a film of a polymer, which is insoluble in the acid environment of the stomach, but soluble in the neutral environment of the small intestine. The delayed-release dosage units can be prepared, for example, by coating a micronutrient composition with a selected coating material. The micronutrient composition may be a tablet for incorporation into a capsule, a tablet for use as an inner core in a "coated core" dosage form, or a plurality of drug-containing beads, particles or granules, for incorporation into either a tablet or a capsule. Preferred coating materials include bioerodible, gradually hydrolysable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract, or slowly erode as the dosage form passes through the gastrointestinal tract, while enzymatically degradable polymers are degraded by bacterial enzymes present in the lower gastrointestinal tract, particularly in the colon. Alternatively, a delayed-release tablet may be formulated by dispersing a drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate and vinyl or enzymatically degradable polymers or copolymers as described above. These hydrophilic polymers are particularly useful for providing a delayed-release matrix. Fatty compounds for use as a matrix material include, but are not limited to, waxes (e.g., carnauba wax) and glycerol tristearate. Once the active ingredient is mixed with the matrix material, the mixture can be compressed into tablets.

A pulsed-release dosage is one that mimics a multiple dosing profile without repeated dosing, and typically allows at least a twofold reduction in dosing frequency as compared with the drug presented as a conventional dosage form (e.g., as a solution or prompt drug-releasing, conventional solid dosage form). A pulsed-release profile is characterized by a time period of no release (lag time) or reduced release, followed by rapid drug release. These can be formulated for critically ill patients using instant micronutrient composition.

The phrases "parenteral administration" and "administered parenterally" as used herein refer to modes of administration other than enteral and topical, such as injections, and include without limitation intravenous, intramuscular, intrapleural, intravascular, intrapericardial, intra-arterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

Certain micronutrient composition disclosed herein, suitable for parenteral administration, comprise one or more subject compositions in combination with one or more pharmaceutically acceptable sterile, isotonic, aqueous, or non-aqueous solutions, dispersions, suspensions or emulsions, or sterile powders, which may be reconstituted into sterile injectable solutions or dispersions just prior to use, and which may contain antioxidants, buffers, bacteriostats, solutes that render the formulation isotonic within the blood of the intended recipient, or suspending or thickening agents.

When an injection product is prepared, micronutrient composition is mixed with an additive such as a pH regulator, a buffer, a stabilizer, an isotonicity agent or a local anesthetic, and the resultant mixture is processed through a routine method, to thereby produce an injection for subcutaneous injection, intramuscular injection, or intravenous injection. Examples of the pH regulator or buffer include sodium citrate, sodium acetate and sodium phosphate; examples of the stabilizer include sodium pyrosulfite, EDTA, thioglycolic acid, and thiolactic acid; examples of the local anesthetic include procaine hydrochloride and lidocaine hydrochloride; and examples of the isotonicity agent include sodium chloride and glucose.

Adjuvants are used to enhance the immune response. Various types of adjuvants are available. Haptens and Freund's adjuvant may also be used to produce water-in-oil emulsions of immunogens.

The phrase "pharmaceutically acceptable" is art recognized. In certain embodiments, the term includes compositions, polymers and other materials and/or dosage forms that are within the scope of sound medical judgment, suitable for use in contact with the tissues of mammals, both human beings and animals, without excessive toxicity, irritation, allergic response or other problem or complication, commensurate with a reasonable benefit-risk ratio.

The phrase "pharmaceutically acceptable carrier" is art recognized, and includes, for example, pharmaceutically acceptable materials, compositions or vehicles, such as a liquid or solid filler, diluent, solvent or encapsulating material involved in carrying or transporting any subject composition from one organ or portion of the body, to another organ or portion of the body. Each carrier must be "acceptable" in the sense of being compatible with the other ingredients of a subject composition, and not injurious to the patient. In certain embodiments, a pharmaceutically acceptable carrier is non-pyrogenic. Some examples of materials that may serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the micronutrient compositions described herein are formulated in a manner such that said compositions will be delivered to a mammal in a therapeutically effective amount, as part of a prophylactic, preventive or therapeutic treatment to overcome the infection caused by corona viruses (irrespective of the type).

In certain embodiments, the dosage of the micronutrient compositions, which may be referred to as therapeutic composition provided herein, may be determined by reference to the plasma concentrations of the therapeutic composition or other encapsulated materials. For example, the blood samples may be tested for their immune response to their corresponding viral load or lack thereof.

The therapeutic micronutrient composition provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled-release dosage forms, site-specific drug delivery, transdermal drug delivery, patch-mediated drug delivery (active/passive), by stereotactic injection, or in nanoparticles.

Expressed in terms of concentration, an active ingredient can be present in the therapeutic compositions of the present invention for localized use via the cutis, intranasally, pharyngolaryngeally, bronchially, intravaginally, rectally or ocularly.

For use as aerosols, the active ingredients can be packaged in a pressurized aerosol container together with a gaseous or liquefied propellant, for example dichlorodifluoromethane, carbon dioxide, nitrogen, propane and the like, with the usual adjuvants such as cosolvents and wetting agents, as may be necessary or desirable. The most common routes of administration also include the preferred transmucosal (nasal, buccal/sublingual, vaginal, ocular and rectal) and inhalation routes.

In addition, in certain embodiments, the subject micronutrient composition of the present application may be lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject micronutrient composition that may be combined with a carrier material to produce a single dose may vary depending upon the subject being treated and the particular mode of administration. Physiological dose levels for mammalian consumption were calculated based on various factors which include type of administration, species dependency and mode of action, such as transdermal vs oral. The range disclosed includes those factors along with scientific calculations. The range may differ within the range as well depending on formulations and species. Drug formulations suitable for these administration routes can be produced by adding one or more pharmacologically acceptable carrier to the agent and then treating the micronutrient composition through a routine process known to those skilled in the art. The mode of administration includes, but is not limited to, non-invasive peroral, topical (for example, transdermal), enteral, transmucosal, targeted delivery, sustained-release delivery, delayed release, pulsed release and parenteral methods. Peroral administration may be administered both in liquid and dry state.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may, for example, contain 0.005-90% w/w, for instance 0.005-50%, 0.005-5% w/w, or 0.01-1.0% w/w, of medicament relative to the total weight of the formulation.

Examples of suitable aqueous and non-aqueous carriers that may be employed in the micronutrient composition include water, ethanol, polyols (such as glycerol, propylene glycol, polyethylene glycol and the like), and suitable mixtures thereof, vegetable oils such as olive oil, and injectable organic esters such as ethyl oleate. Proper fluidity may be maintained, for example by the use of coating materials such as lecithin, by the maintenance of the required particle size in the case of dispersions, and by the use of surfactants.

What is claimed is:

1. A pharmaceutical composition, comprising:
   a Rosemary extract, Fenugreek, Cassia nomane, 3'3-di indolylmethylene, Zinc, Phosphatidylserine, Vitamin D, Vitamin C, Niacin, Theanine, Aspartic acid and Arginine.

2. The pharmaceutical composition of claim 1, further comprising Dehydroepiandrosterone (DHEA) in combination with the Rosemary extract, Fenugreek, Cassia nomane, 3'3-di indolylmethylene, Zinc, Phosphatidylserine, Vitamin D, Vitamin C, Niacin, Theanine, Aspartic acid and Arginine to form a Mix 1.

3. The pharmaceutical composition of claim 1, wherein the Rosemary extract, Fenugreek, Cassia nomane, 3'3-di indolylmethylene, Zinc, Phosphatidylserine, Vitamin D, Vitamin C, Niacin, Theanine, and Aspartic acid form a Mix A.

4. The pharmaceutical composition of claim 2, wherein the Mix 1 contains the Rosemary extract at 1 mg-6,000 mg, Fenugreek extract at 1 mg-50,000_mg and Fenugreek seed powder at 2 mg-8,000 mg, Cassia nomane seed extract powder at 1 mg to 1,000 mg and Cassia nomane dry extract at 1 mg-300 mg, 3'3-di indolylmethylene at 1 mg-800 mg, Zinc at 0.1 mg-1,000 mg, Phosphatidylserine at 1 mg-1,500 mg, Vitamin D at 20 IU-10,000 IU, Vitamin C at 10 mg-50,000 mg, Niacin 1 mg-3,000 mg, Theanine at 0.1 mg-10,000 mg, Aspartic acid at 10 mg-10,000 mg, Arginine at 10 mg-50,000 mg and Dehydroepiandrosterone (DHEA) at 1 mg-500 mg.

5. The pharmaceutical composition of claim 3, wherein the Mix A contains the Rosemary extract at 1 mg-6,000 mg, Fenugreek extract at 1 mg-50,000 mg and Fenugreek seed powder at 2 mg-8,000 mg, Cassia nomane seed extract powder at 1 mg to 1,000 mg and Cassia nomane dry extract at 1 mg-300 mg, 3'3-di indolylmethylene at 1 mg-800 mg, Zinc at 0.1 mg-1,000 mg, Phosphatidylserine at 1 mg-1,500 mg, Vitamin D at 20 IU-10,000 IU, Vitamin C at 10 mg-50,000 mg, Niacin at 1 mg-3,000 mg, Theanine at 0.1 mg-10,000 mg, Aspartic acid at 10 mg-10,000 mg and Arginine at 10 mg-50,000 mg.

6. The pharmaceutical composition of claim 4, wherein the Mix 1 increases testosterone levels in cells.

7. The pharmaceutical composition of claim 4, wherein the Mix 1 shows inhibitory effect on RANTES.

8. The pharmaceutical composition of claim 4, wherein the Mix 1 decreases IL 6 secretion.

9. The pharmaceutical composition of claim 4, wherein the Mix 1 decreases the contraction of smooth muscle cells.

10. A pharmaceutical composition, comprising of;
    a Mix 1 containing a Rosemary extract at 1 mg-6,000 mg, Fenugreek extract at 1 mg-50,000 mg and Fenugreek seed powder at 2 mg-8,000 mg, Cassia nomane seed extract powder at 1 mg to 1,000 mg and Cassia nomane dry extract at 1 mg-300 mg, 3'3-di indolylmethylene at 1 mg-800 mg, Zinc at 0.1 mg-1,000 mg, Phosphatidylserine at 1 mg-1,500 mg, Vitamin D at 20 IU-10,000 IU, Vitamin C at 10 mg-50,000 mg, Niacin at 1 mg-3,000 mg, Theanine at 0.1 mg-10,000 mg, Aspartic acid at 10 mg-10,000 mg, Arginine at 10 mg-50,000 mg and Dehydroepiandrosterone (DHEA) at 1 mg-500 mg.

11. The pharmaceutical composition of claim 10, wherein the Mix 1 improves men's health.

12. The pharmaceutical composition of claim 10, wherein the Mix 1 increases testosterone levels in cells.

13. The pharmaceutical composition of claim 10, wherein the Mix 1 shows inhibitory effect on RANTES.

14. The pharmaceutical composition of claim 10, wherein the Mix 1 decreases IL 6 secretion.

15. A pharmaceutical composition, comprising of:
    a Mix A containing a Rosemary extract at 1 mg-6,000 mg, Fenugreek extract at 1 mg-50,000 mg and Fenugreek seed powder at 2 mg-8,000 mg, Cassia nomane seed extract powder at 1 mg to 1,000 mg and Cassia nomane dry extract at 1 mg-300 mg, 3'3-di indolylmethylene at 1 mg-800 mg, Zinc at 0.1 mg-1,000 mg, Phosphatidylserine at 1 mg-1,500 mg, Vitamin D at 20 IU-10,000 IU, Vitamin C at 10 mg-50,000 mg, Niacin 1 at mg-3,000 mg, Theanine at 0.1 mg-10,000 mg, Aspartic acid at 10 mg-10,000 mg and Arginine at 10 mg-50,000 mg.

16. The pharmaceutical composition of claim 15, wherein the Mix A reduces cytokine pro-inflammatory effect in cells.

17. The pharmaceutical composition of claim 15, wherein the Mix A improves men's health.

* * * * *